(12) United States Patent
Venkatachalam

(10) Patent No.: US 12,036,080 B1
(45) Date of Patent: Jul. 16, 2024

(54) DENTAL CLEANING METHODS AND DENTAL CLEANING DEVICES AND ACCESSORIES

(71) Applicant: Seetharaman Venkatachalam, Montville, NJ (US)

(72) Inventor: Seetharaman Venkatachalam, Montville, NJ (US)

(*) Notice: Subject to any disclaimer, the term of this patent is extended or adjusted under 35 U.S.C. 154(b) by 812 days.

(21) Appl. No.: 17/172,023

(22) Filed: Feb. 9, 2021

Related U.S. Application Data

(60) Provisional application No. 62/972,766, filed on Feb. 11, 2020.

(51) Int. Cl.
| | | |
|---|---|---|
| A61C 17/22 | (2006.01) | |
| A46B 9/00 | (2006.01) | |
| A61C 17/26 | (2006.01) | |
| A61C 17/34 | (2006.01) | |
| A61K 8/9789 | (2017.01) | |
| A61K 8/9794 | (2017.01) | |
| A61Q 11/00 | (2006.01) | |

(52) U.S. Cl.
CPC ............ *A61C 17/225* (2013.01); *A46B 9/005* (2013.01); *A61C 17/26* (2013.01); *A61C 17/34* (2013.01); *A61K 8/9789* (2017.08); *A61K 8/9794* (2017.08); *A61Q 11/00* (2013.01); *A61C 2201/00* (2013.01); *A61C 2204/002* (2013.01); *A61K 2800/87* (2013.01)

(58) Field of Classification Search
CPC ... A61C 17/16; A61C 17/18; A61C 17/22–40; A61C 2201/00; A61K 8/9794; A61K 2800/87; A46B 9/005
USPC .................................................. 15/21.1
See application file for complete search history.

(56) References Cited

U.S. PATENT DOCUMENTS

| | | | | |
|---|---|---|---|---|
| 4,134,169 A | * | 1/1979 | Sinclair ................. | A61C 17/38 |
| | | | | 601/142 |
| 6,490,747 B1 | * | 12/2002 | Metwally ............. | A61C 17/222 |
| | | | | 15/207.2 |
| 2003/0111091 A1 | * | 6/2003 | Hotta .................... | A61C 15/047 |
| | | | | 132/322 |

FOREIGN PATENT DOCUMENTS

DE  202009003421 U1 * 6/2009  ......... A61C 17/3418

OTHER PUBLICATIONS

Translation of DE202009003421 (Year: 2009).*

* cited by examiner

*Primary Examiner* — Tom Rodgers

(57) ABSTRACT

A harvested botanic offshoot has a first end with a portion thereof stripped of bark forming a botanic cleaning component that is adapted for insertion into a human mouth for dental cleaning. A proximal end of the offshoot can be carved down in size and releasably installed in a socket or internal channel inside a dental cleaning assembly. A motor inside the dental cleaning assembly can vibrate, oscillate or rotate the botanic cleaning component inside a user's mouth. The dental cleaning assembly has an opening arranged to allow at least a portion of the botanic cleaning component to extend outside the body portion of the dental cleaning assembly.

12 Claims, 13 Drawing Sheets

DENTAL CLEANING METHODS AND DENTAL CLEANING DEVICES AND ACCESSORIES

RELATED APPLICATIONS

This application claims the benefit of U.S. Provisional Patent Application No. 62/972,766 filed on Feb. 11, 2020; which is herein incorporated by reference in entirety.

TECHNICAL FIELD

The present invention relates to dental cleaning methods, and dental cleaning devices and accessories.

BACKGROUND

Toothbrushes have been used to apply a mildly abrasive toothpaste on teeth to clean the teeth and promote good dental hygiene. This regimen can remove plaque, residual food particles and also stimulate the gums. Some toothpastes have been supplemented with a whitening agent to brighten teeth.

A typical toothbrush has a handle with a group of bristles projecting perpendicularly from the distal end of the brush handle. The brush is typically used by moving the bristles across the teeth (right to left) and along the length of the teeth (up-and-down).

Electric toothbrushes have a case containing a motor that can drive a replaceable toothbrush. In some cases, the motor axially reciprocates the brush's handle to facilitate brushing across the teeth. In other cases, the bristles of the toothbrush are mounted on a disk that is rotated alternately to oscillate between a clockwise and counterclockwise direction.

Neem is a tree that is believed to offer therapeutic benefits (sometimes referred to as ayurvedic properties). Neem twigs have been used for respiratory ailments, urinary disorders, intestinal and colon problems, etc. Also, neem extracts are believed to be antiseptic. These extracts have been used as an additive in toothpaste or as a flavoring for the bristles of toothbrushes. In some cultures, one end of a neem twig or branch is stripped of its bark, chewed, and the masticated core is then used as a toothbrush. In this specification neem twigs are considered a botanic, although clearly a large variety of plants are botanic as well.

The present application seeks to improve upon the current state of art and provide a more natural and environmentally friendly system and method for providing dental hygiene.

SUMMARY

The present application relates to a dental cleaning system that comprises a botanical cleaning component that has a cleaning section which has been stripped of bark and has an insertion section. A dental cleaning assembly is comprised of the following components: a housing having a power source; a motor disposed within the said housing; an insertion channel in mechanical communication with the motor; a head portion having a pair of arms; and an operating switch. A portion of the insertion section of the botanic cleaning component can be inserted through a front slot disposed between the pair of arms of the head portion and into the insertion channel which is in mechanical communication with the motor. The head portion can further include a backside slot. The arms of the head portion are also configured to brace a portion of the inserted botanical section of the dental cleaning component between the arms.

In some instances, the botanical cleaning component can snap into place between the two arms.

The dental cleaning component can contain a liquid portion by weight equal to or greater than 5%. The dental cleaning component can also have a liquid portion by weight equal to or greater than 10%, or have a liquid portion by weight equal in range of 10% to 20%. In some instances, the dental cleaning component can have a liquid portion by weight up to 30%.

The insertion section of the dental cleaning component includes an end section that has a diameter less than the insertion section, wherein the motor is configured to drive the dental cleaning component in a vibrating, oscillating or rotational manner. The direction of the rotational, vibrating or oscillating manner includes: up and down, right to left, in and out motions, as well as back and forth (reversing direction).

The botanical cleaning component is formed from one of the following plants: one of the varieties of Neem, one of the varieties of Eucalyptus, one of the varieties of Bamboo, and one of the varieties of Melaleucas. The cleaning section of the dental cleaning component can be partially flattened from an original harvested shape from one of the above listed botanicals.

The method of cleaning teeth is comprised of the following steps of: inserting a botanical cleaning component into a dental cleaning assembly; turning the dental cleaning assembly on, such that it causes a portion of the botanical cleaning component to oscillate or rotate; and applying the vibrating, oscillating or rotating portion of the botanical cleaning component to a user's teeth.

An additional step of preparing a cleaning section of the botanical cleaning component is roughening up a portion thereof. The roughening step includes biting portions of the cleaning section sufficient to allow juice from the botanical cleaning component to excrete during the applying or application process. The roughening step includes pressing a portion of the cleaning section between a pressing tool sufficient to allow juice from the botanical cleaning component to excrete during the application process.

The method of producing botanical cleaning components comprises the following steps of: harvesting from a plant an offshoot or stem; stripping from a portion of the offshoot or stem bark to form a cleaning section; and reducing another portion of the offshoot or stem to a specified diameter and length using a cutting tool to form an insertion section. The insertion section is machined or formed to be inserted into a dental cleaning assembly.

The method of producing a botanical cleaning component can further include the step of packaging and transporting the botanical components to ensure the botanical components have a liquid portion by weight in the range of 5% to 30%. Alternatively, the botanical cleaning components can be packaged and shipped such that they have a liquid portion by weight of greater than 10%.

Yet another step can include roughening the cleaning section of the botanical. This can be done by using a pressing tool or alternatively a user can bite or use their teeth to roughen the cleaning section surface, which allows the botanical juice to better excrete during the cleaning process.

Of course, the present invention is not limited to the above features and advantages. Those of ordinary skill in the art will recognize additional features and advantages upon reading the following detailed description, and upon viewing the accompanying drawings.

DETAILED DESCRIPTION

Embodiments of the present invention are directed to an environmentally friendly and natural dental cleaning system and method.

Figure 1A:
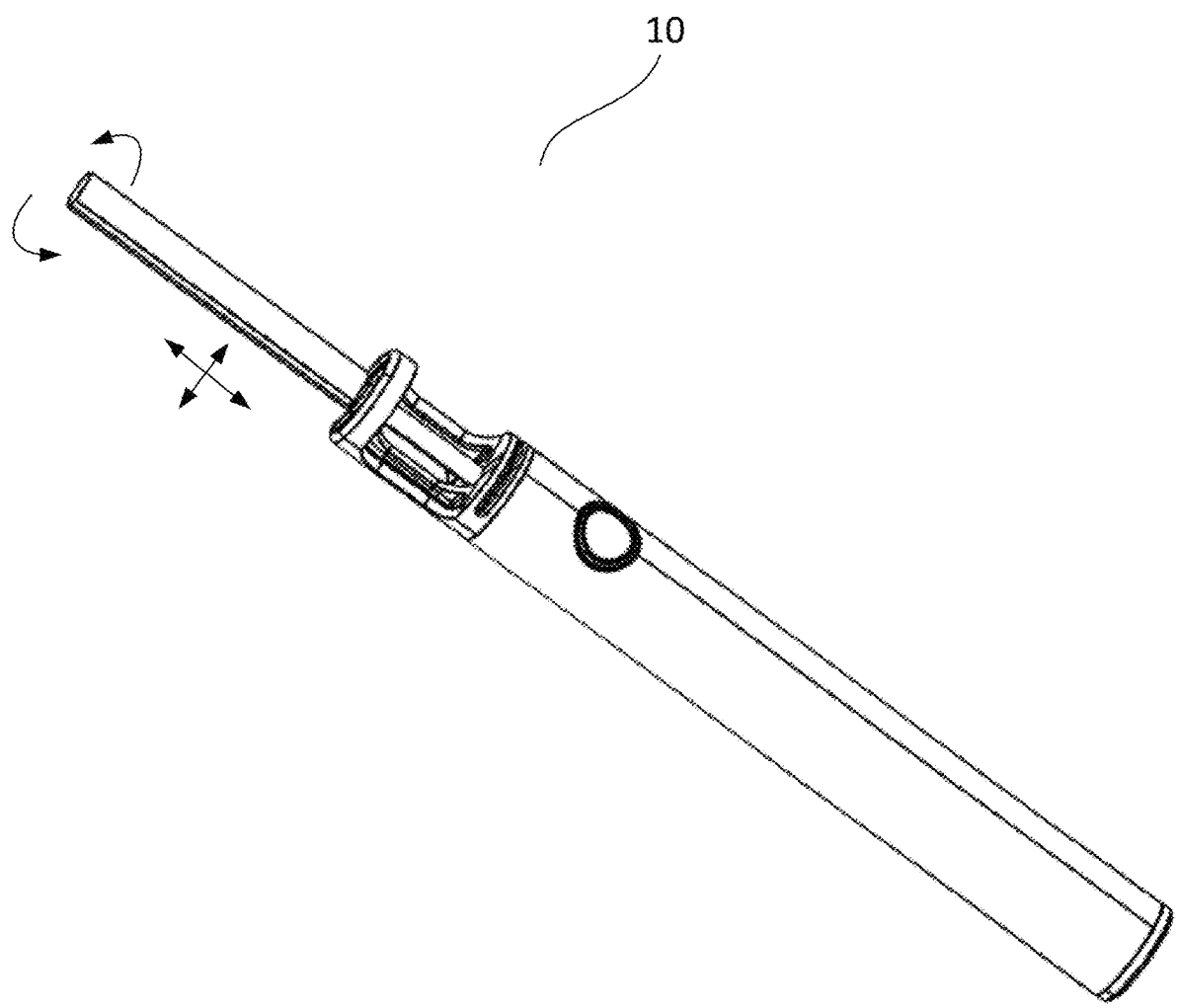
FIGS. 1A-G illustrate various views of a dental cleaning system.
Figure 1B:
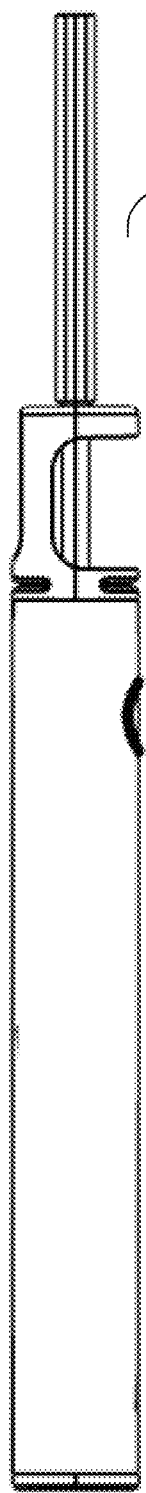
Figure 1C:
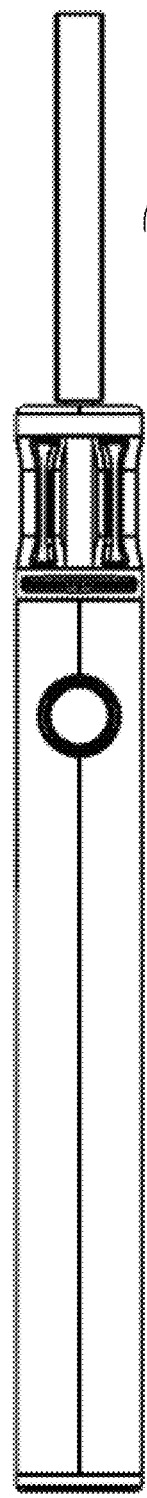
Figure 1D:
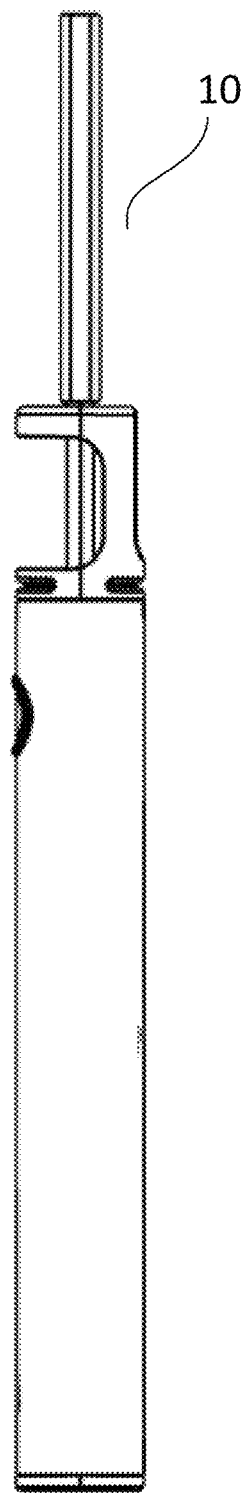
Figures 1E, 1F, 1G:
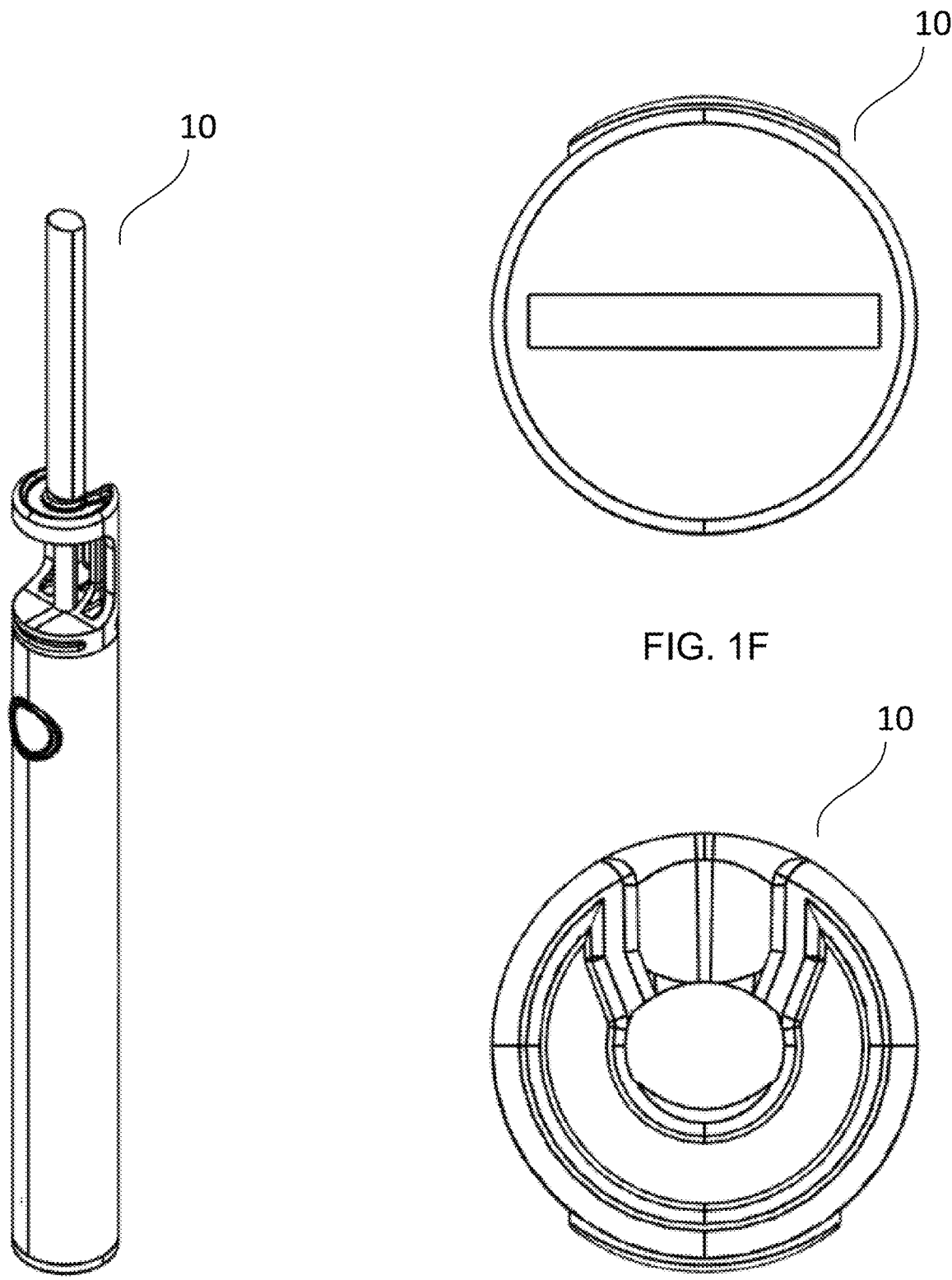

FIGS. 1A-G illustrate various views of a dental cleaning system 10, including a perspective view in FIG. 1A including illustrating the various directions the dental cleaning assembly 200 can vibrate, oscillate or rotate botanic cleaning component 100. FIGS. 1B-D illustrate front, right and left side views of dental cleaning system 10. FIG. 1E is another perspective view. FIGS. 1F-G are bottom and top view of dental cleaning system 10.

Figure 2:
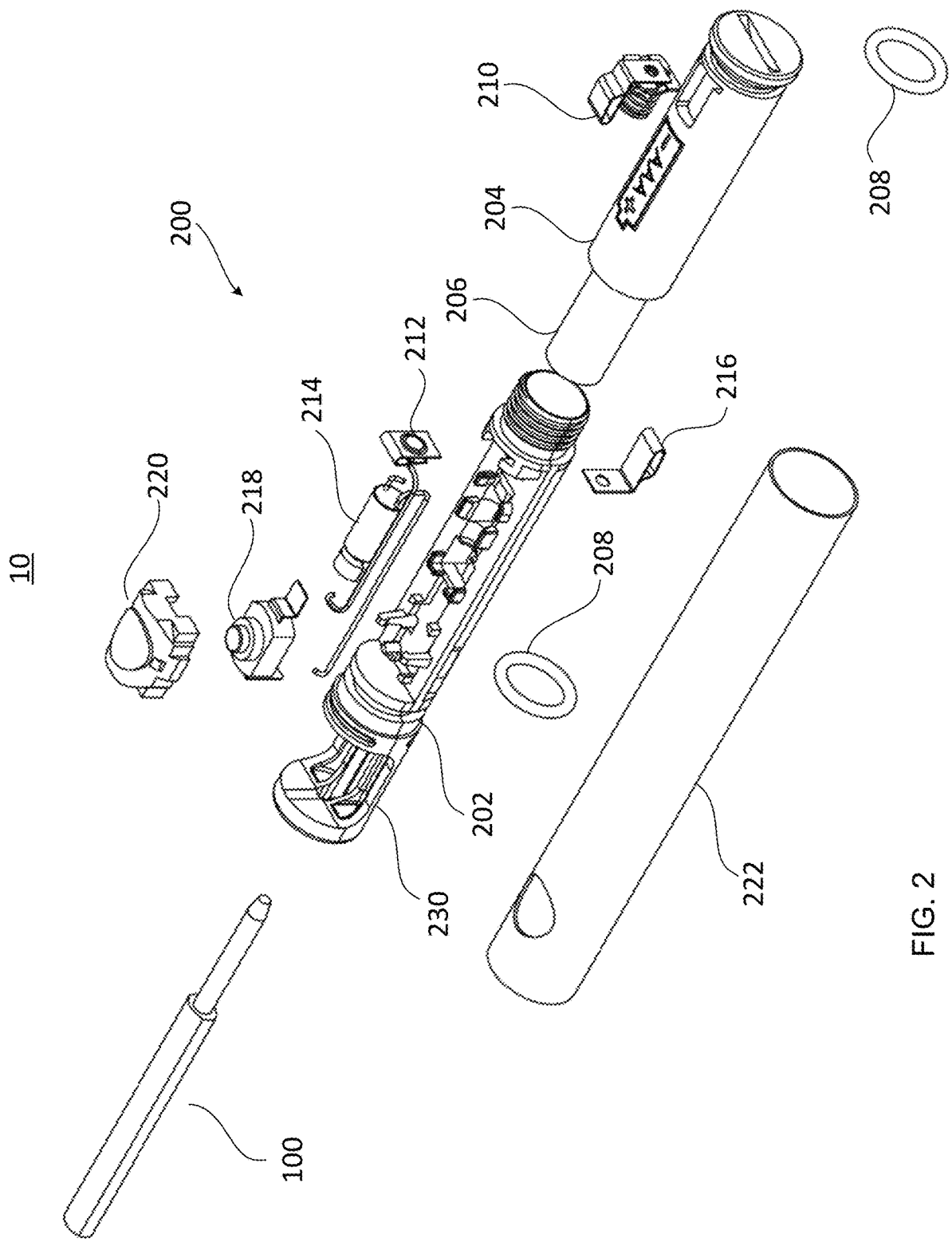
FIG. 2 is an exploded view of the dental cleaning system of FIGS. 1A-G.

FIG. 2 illustrates an exploded view of dental cleaning system 10, which includes a dental cleaning assembly portion 200 and a dental cleaning component 100. The dental cleaning assembly includes a body portion 202 that is configure to be attached to a battery holder 204, that can house a replaceable or rechargeable battery 206. O-rings 208 help keep the internal components of the dental cleaning assembly 200 free of dust and moisture. A negative battery contact 210 is position on one end of the battery holder 204 and electrically interfaces with the battery 206. Similarly, a positive battery contact 212 electrically interfaces with the battery 206 and in particular the positive terminal of the battery 206. The battery 206 provides power to drive the motor 214, which can be a vibrating or oscillating motor configure to drive the cleaning component 100 in a circular rotating manner, an oscillating circular manner, an up-and-down manner, or a side-to-side manner. A negative housing contact 216 acts as a ground. An electrical switch 218 is provided to switch between various modes, such on/off, circular, up-and-down, or side-to-side. In some instances, the frequency of the oscillations or rotations can be increased. A button 220 is configured to be external facing for a user to depress or interact with that interacts with the electrical switch 218. Although a pushbutton is shown, it is known that a sliding, rotatory, or other style switch could be used. An external tube 222 slides over the body portion 202 and battery holder 204 to cover and help seal in many of the components described above. The tube 222 can be made from aluminum and help act as a ground for the electrical components and battery. It can also include a head portion 230 for guiding and attaching the botanic cleaning component 100.

Figures 3A, 3B, 3C:
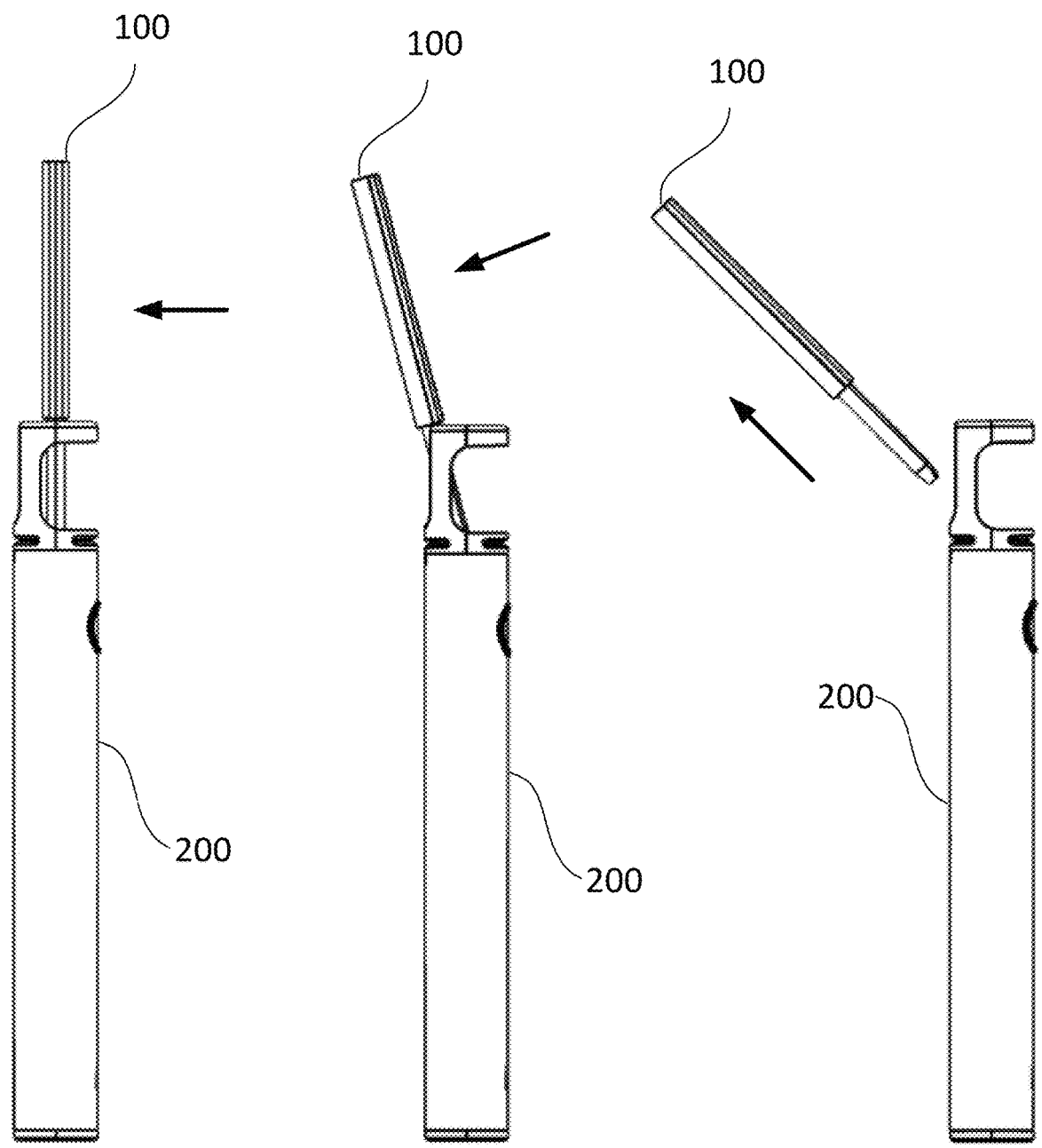
FIGS. 3A-C illustrates removing the botanic cleaning component from the dental cleaning assembly.

FIGS. 3A-C illustrates removing the botanic cleaning component 100 from the dental cleaning assembly 200. A user applies a sideways force as shown in FIG. 3A, which continues into an angled force as the botanic component begins to rotate or bend with respect to the dental cleaning assembly 200 in FIG. 3B, where eventually the botanic cleaning component 100 can be pulled out and completely removed as shown in FIG. 3C. The botanic cleaning component is meant to be replaceable and will be discussed in further detail below.

Figure 4A:
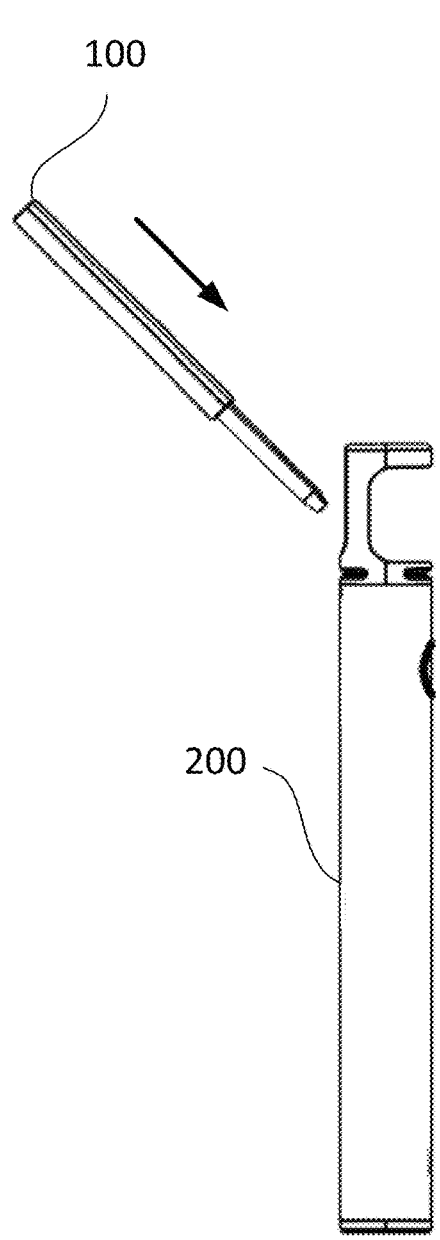
FIGS. 4A-C illustrates loading a botanic cleaning component into the dental cleaning assembly.
Figure 4B:
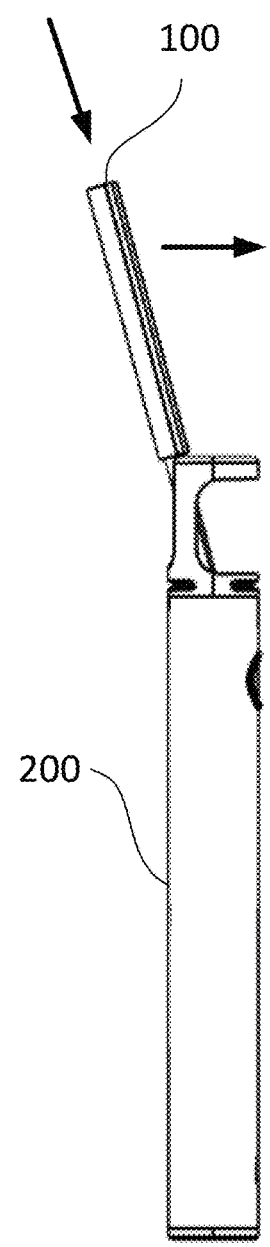
Figure 4C:
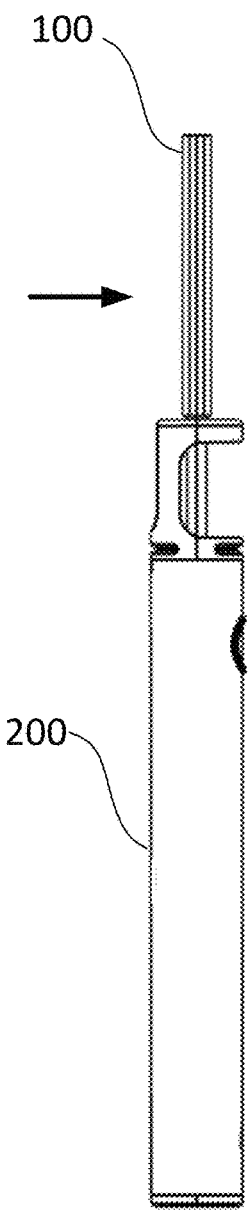
Figure 6A:
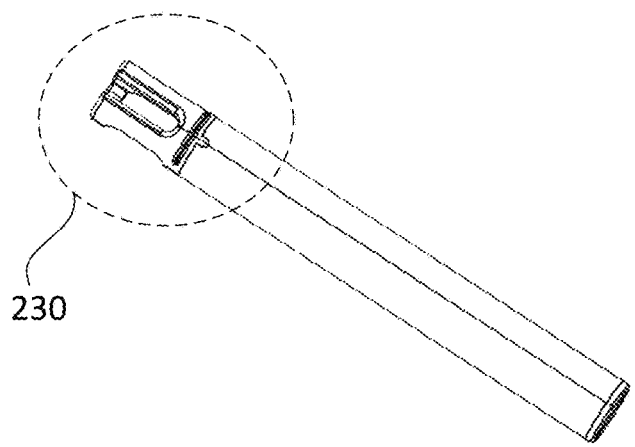
FIGS. 6A-C illustrate various views of the upper portion of the dental cleaning assembly.
Figure 6C:
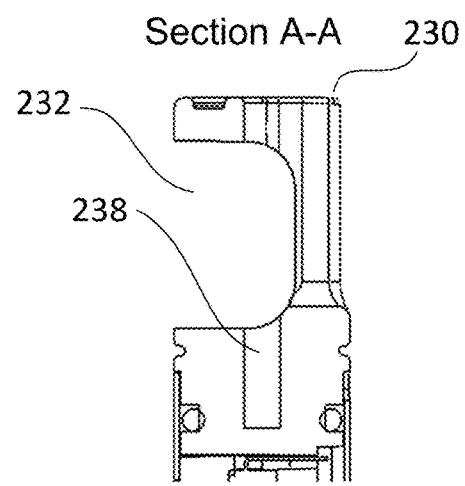
Figure 6B:
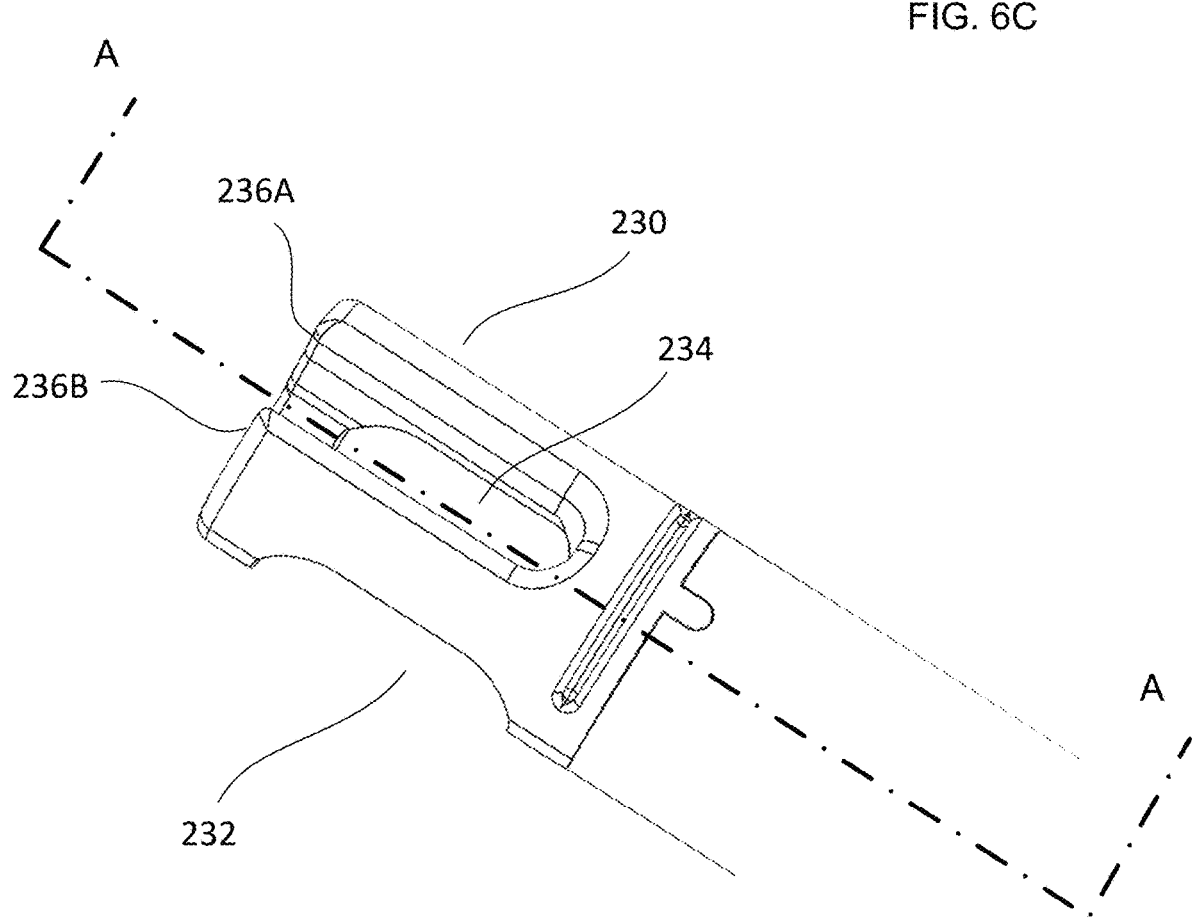

FIGS. 4A-C illustrates loading a new botanic cleaning component 100 into the dental cleaning assembly 200. Similar to the removing steps shown in FIGS. 3A-C the loading steps are effectively in reverse, where the botanic cleaning component 100 is inserted into the dental cleaning assembly 200 at angle, where the end begins to be inserted into an internal channel 238, shown in FIG. 6C. Once the botanic cleaning component 100 has begun to be inserted into the internal channel 238 it begins to rotate upright and align vertically with the dental cleaning assembly 200. Finally, it is locked or snapped into place between slot arms 236A and 236B of head portion 230 shown in FIG. 6B. The slot arms are formed in part by the front slot 234, which is where the botanic cleaning component is initially inserted into. Once upright the user can turn the dental cleaning assembly 200 on using the button 220. Also shown in the embodiment and labeled in FIG. 6B is a backside slot 232. This backside slot or opening is optional, but allows the user to see the botanic cleaning component 100 from multiple sides.

Figure 5:
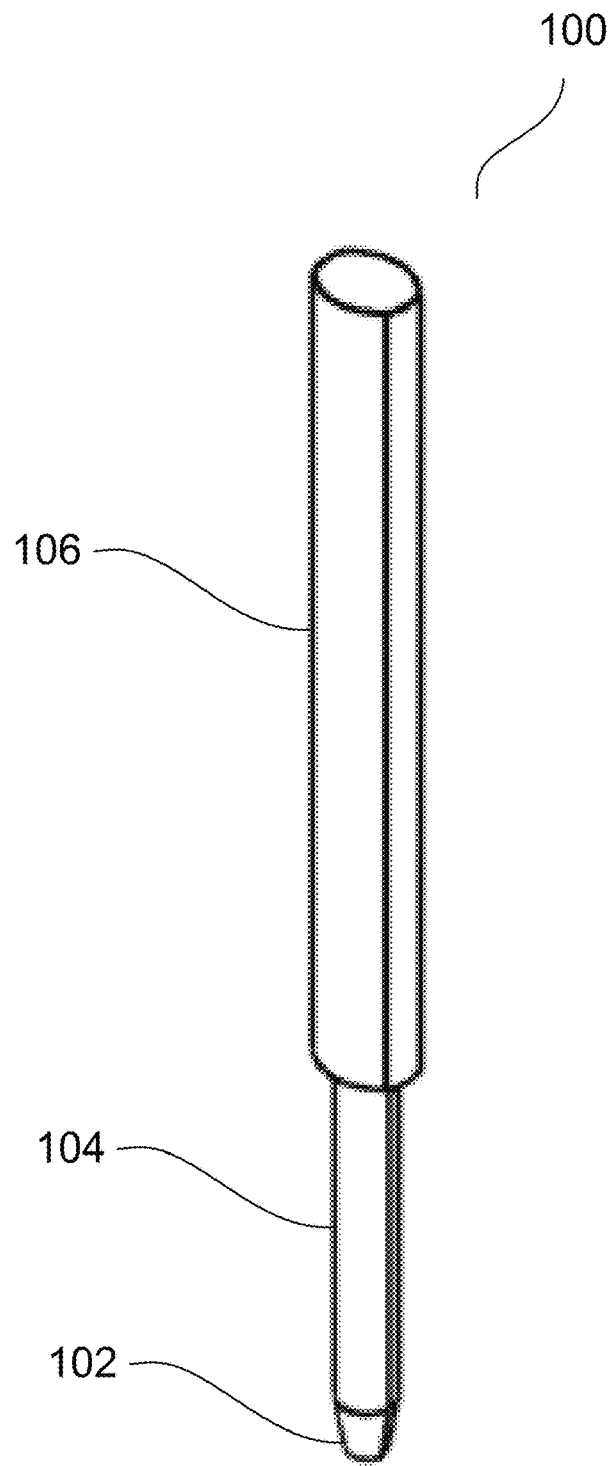
FIG. 5 illustrates a botanic cleaning component.

FIG. 5 illustrates a botanic cleaning component 100. In at least one embodiment the botanic cleaning component 100 is formed from a Neem twig or branch. As noted above, the Neem plant has been known to have dental properties when chewed or masticated. The botanic cleaning component 100 is processed into two or three sections. Section 106 is processed and intended to be used against the user's teeth, section 104 is configured to be inserted and attached to the dental cleaning assembly and optionally section 102, which is the end or tip portion of 104 is processed to aid in the inserting step.

For example, section 104 is machined to a circular shape and particular diameter that is sized to coincide with the diameter of the internal channel 238 and the gap formed between slot arms 236A and 236B. Ideally, the diameter of the processed section 104 of 100, is oversized enough to be press-fit into the internal channel 238 and optionally press-fit into the slot or gap disposed between slot arms 236A or 236B. The end or tip portion 102 is machined or formed to have an initial smaller diameter to assist in initially inserting the botanic cleaning component 100 into 238 as noted. This machined end can have a chamfer, a rounded edge, or other similar features, which aid in entering the internal channel. The length and width of both the insertion section 102 and tip or end 104 can vary.

Section 106 is initially processed by stripping off any bark and in some embodiments can be partially flattened. This optional flattening can be accomplished with a hammer or pressing tool. With the bark stripped off the softer internal components as well as the botanic juice or sap become more exposed. Alternatively, section 106 can be stripped of bark initially and when the end user goes to use it, the user can then bite on this section or use a pressing tool, such as noted below, to aid in the release of the botanic juice disposed therein.

As the user places section 106 against their teeth, the oscillating or rotating of 100 allows the softer internal portion of the twig to abrasively clean the user's teeth, while causing the sap or juice to excrete onto the teeth. The botanic juice or sap of the Neem plant is known to have positive dental hygiene benefits and through the vibrating, oscillating or rotary process provided by 200 enables that juice to be disbursed throughout the mouth of the user, when using the dental cleaning system 10 for cleaning teeth. Neem juice is comprised of the natural medicinal components from the Neem plant and an aqueous component that is primarily comprised of water. Similarly, other botanic juice is comprised of the natural medicinal components from the particular botanic plant and an aqueous component that is primarily comprised of water. Some of these botanic plants with desired properties could include bamboo, eucalyptus, miswak, Azadirachta indica, or *Salvadora persica* plants.

In one embodiment it is desirable to provide replaceable botanic cleaning components 100 formed from Neem twigs or offshoots comprising the liquid portion (the juice or sap) to be in the range of between 5% to 15% by weight. In some embodiments it is preferred to have at least 10% and up to 20%, have at least 10% and up to 30% of the liquid portion by weight. Each processed botanic cleaning component is generally intended to be used for a single brushing or cleaning use and then disposed of thereafter.

Once the bark is stripped from the botanic twig and it is processed having an end section configured to be inserted into 200, the liquid portion, which in some instances is comprised of mostly water content, can begin to evaporate from the processed botanic cleaning component 100. As a result, it is desirable to have a higher percentage of weight by liquid, even upwards of 60% by weight, as some of the water content of the liquid portion can evaporate through the distribution process to the end consumer. It is also important to not have too high of liquid content and seal the botanic cleaning components 100, in order to avoid the growth of mold or other fungus.

Figure 7:
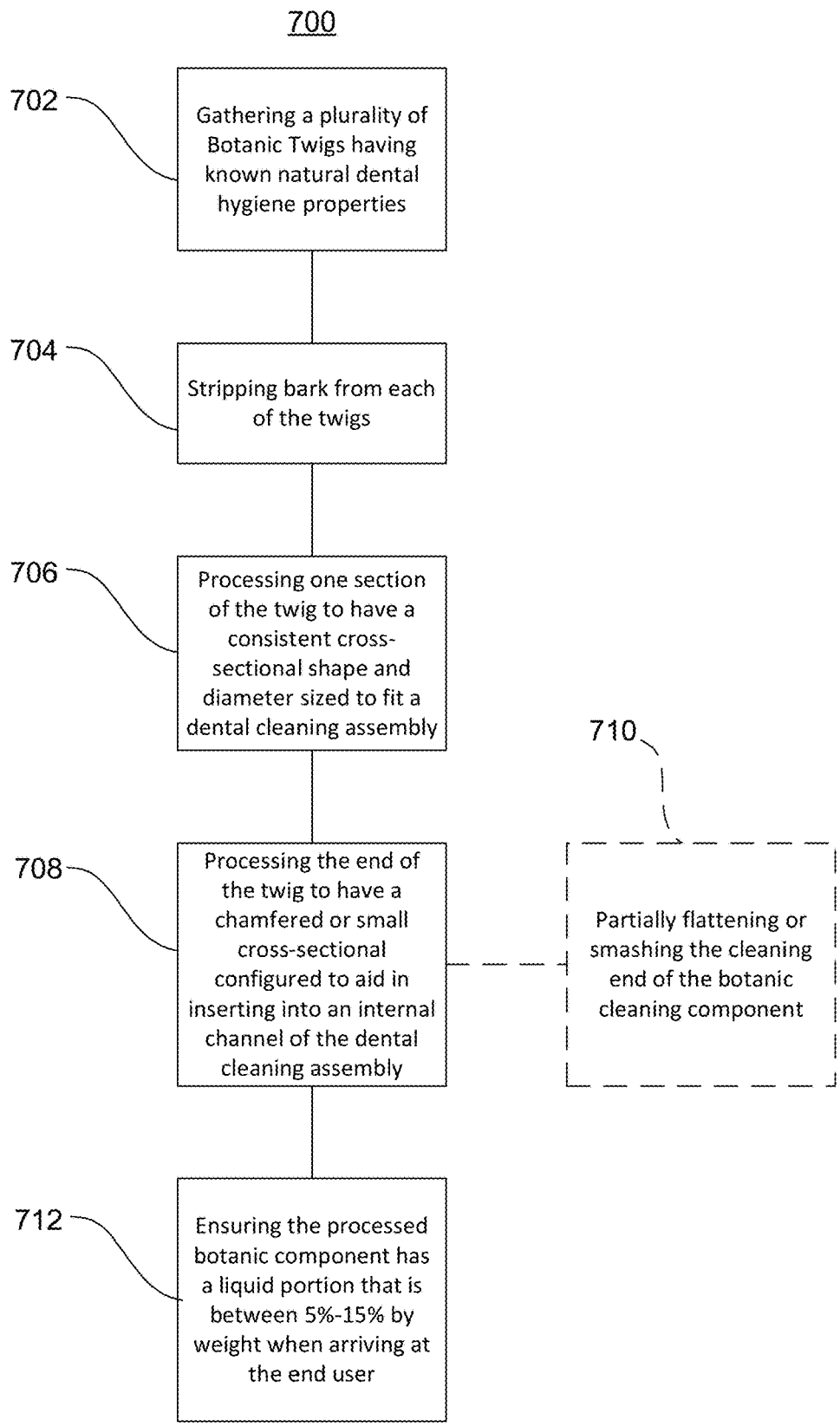
FIG. 7 is a method of preparing a botanic cleaning component.

FIG. 7 is a method 700 of preparing a botanic cleaning component comprising the step 702 of gathering a plurality of botanic twigs, offshoots or branches having known natural dental hygiene properties. These can include Neem plants, Bamboo plants, Melaleuca plants, and other varieties. Once a plurality of twigs are gathered, in step 704 the bark is stripped from each of the twigs where applicable. One end of each of the twigs is processed in step 706 to have a particular shape and diameter that is sized to interface with a dental cleaning assembly, such as 200 described above. The end portion of the processed section, can be further processed to have a chamfer or smaller diameter section in step 708 to aid in being configured to be more easily insertable into an internal channel of a dental cleaning assembly. An optional step 710 includes partially smashing or flattening section of the botanic cleaning component to be used for cleaning. This flattening or smashing can be done using a hammer, pliers, vise grips or other similar methods meant to partially change the cross-sectional shaped into a flatter shape. Finally step 712 ensures that during the processing and shipping that a desired botanic juice or liquid by weight ratio is maintained, such that the end user receives the botanic cleaning component in the desired range, which could be between 5% to 15% liquid by weight, greater than 10% or between 5% to 30% by way of example.

Figure 8:
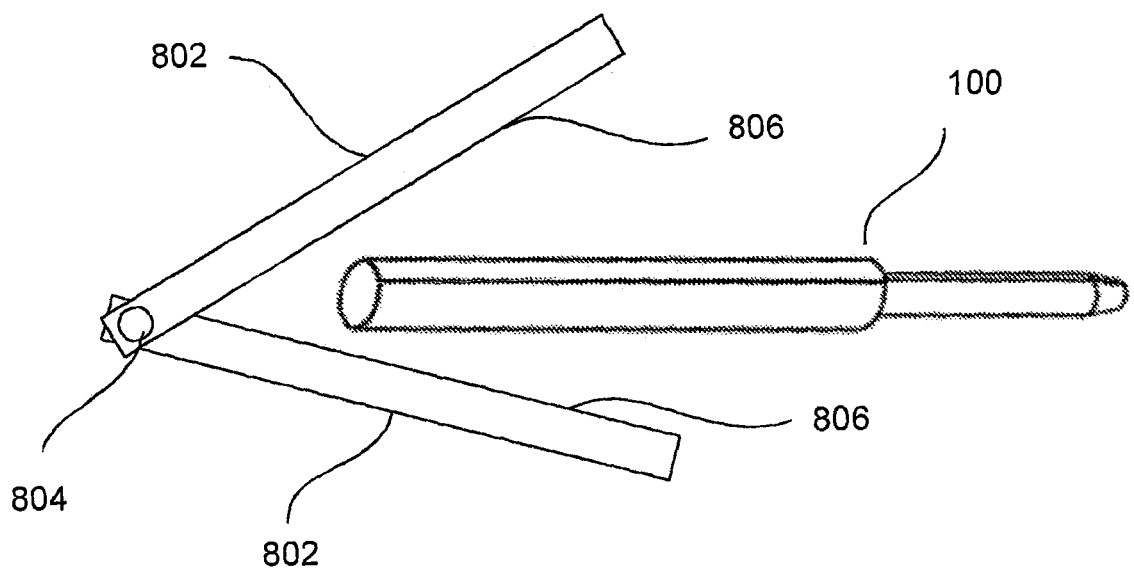
FIG. 8 illustrates a crushing tool for use with the botanic cleaning component.

FIG. 8 illustrates a crushing tool 800 for use with the botanic cleaning component 100. The crushing tool 800 shown has two arms 802 that can rotate about pivot element 804. On the inner surface 806 of each arm there can be features, such as grit, grooves, protrusions and so forth that aid in penetrating the surface of the botanic cleaning component 100 in a manner to allow the natural juice disposed within 100 to excrete and especially during the teeth cleaning process as part of using the dental cleaning system 10.

Once a user is done using the botanic cleaning component 100 to clean their teeth, they can also use it to scrape and clean their tongue. The botanic cleaning component 100 can also be run over the user's gums, so as to apply the natural botanic juice directly to the user's gums. These two additional measures are optional, but meant to promote overall dental health.

Once a user is done using the botanic cleaning component 100 to clean their teeth it can be composted as a natural composting product, thus eliminating the need to go to a landfill and reducing throw-away disposable plastic components often used in the dental hygiene space. These disposable plastic components are often not recycled and contribute negatively to landfills, oceans and rivers, similar to most plastic that is not-recycled. Thus, another advantage of the systems and methods discussed herein are that through harvesting a naturally grown botanic product, use of the product and composting, both physical and carbon-emission produced waste are reduced.

Figure 9A:
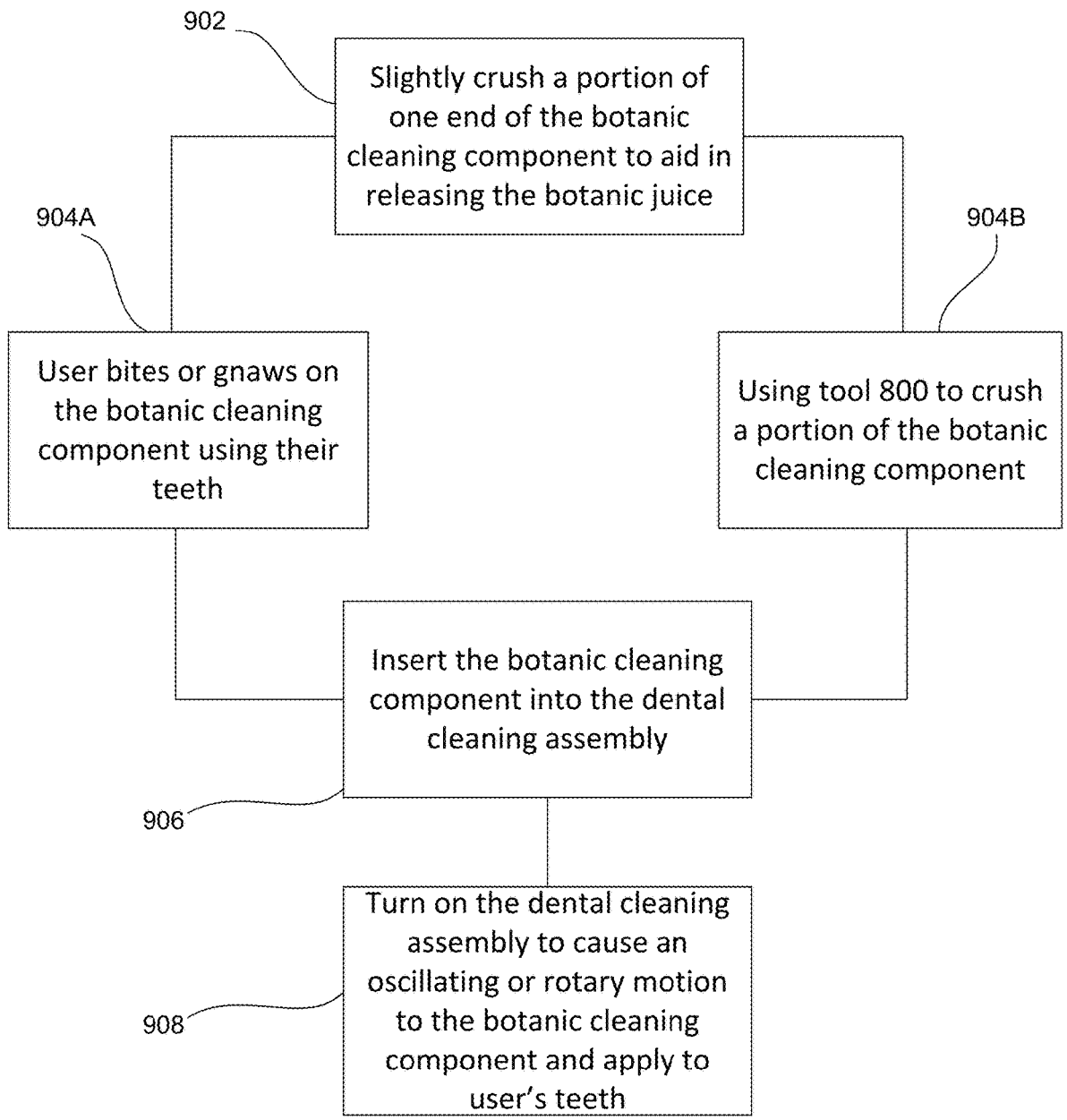
FIGS. 9A-B illustrate various methods for cleaning a user's teeth.
Figure 9B:
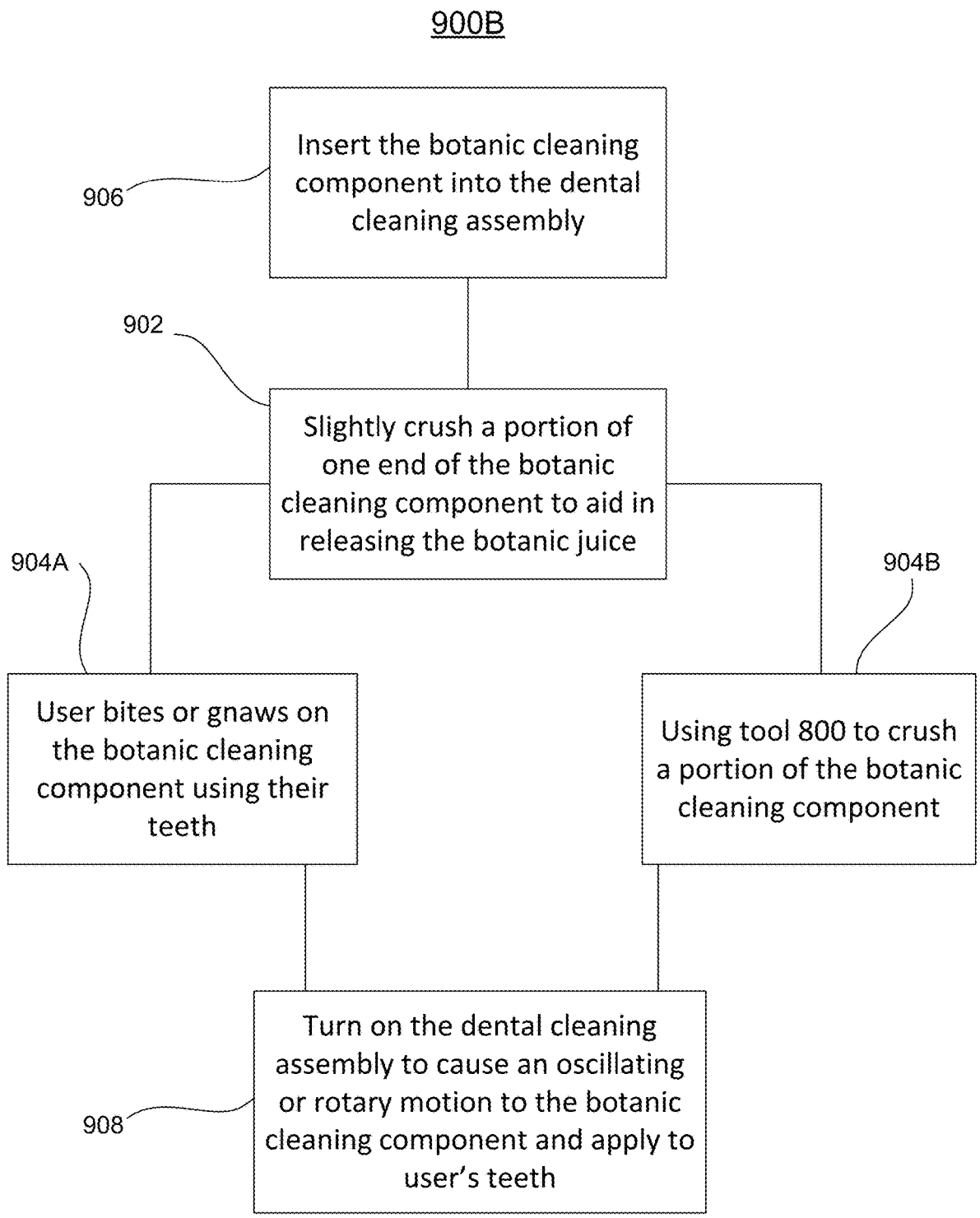

FIGS. 9A-B illustrate flow charts showing a method of preparing the dental cleaning component 100, such as using the tool 800 or alternatively where the user bites portions of the dental cleaning component using their teeth. Once the exterior surface of 100 is somewhat roughened and smashed, such that natural juice disposed within the botanic cleaning component can better excrete. The roughening or smashing can also expose bristle-like fibers that can aid in scrubbing or cleaning teeth, as they act like an abrasive feature. The user can then insert 100 into the dental cleaning assembly 200 where 100 can be oscillated or rotated using the dental cleaning assembly 200. This vibrating, oscillating or rotating motion helps the botanic cleaning component 100 clean a user's teeth when applied. Similar to using an electric toothbrush the rapid motion of the cleaning component can help remove plaque, residue and other food components from the user's teeth, while at the same time excreting and disseminating the natural juice from the botanic cleaning component onto the user's teeth and gums, where the user can benefit from the natural medical properties.

As shown in the each of the flow charts the steps 902, 904A or 904B, 906, and 908 can be reordered. For example, the step 902 of slightly crushing or preparing the surface of 100 can happen before 906 inserting the botanic cleaning component, such as in 900A, into the dental cleaning assembly or after such as in 900B. How the botanic cleaning component is prepared can be done directly by a user, utilizing their own teeth, or alternatively using a tool, such as 800 taught above, to prepare it before brushing.

Figures 10A, 10B:
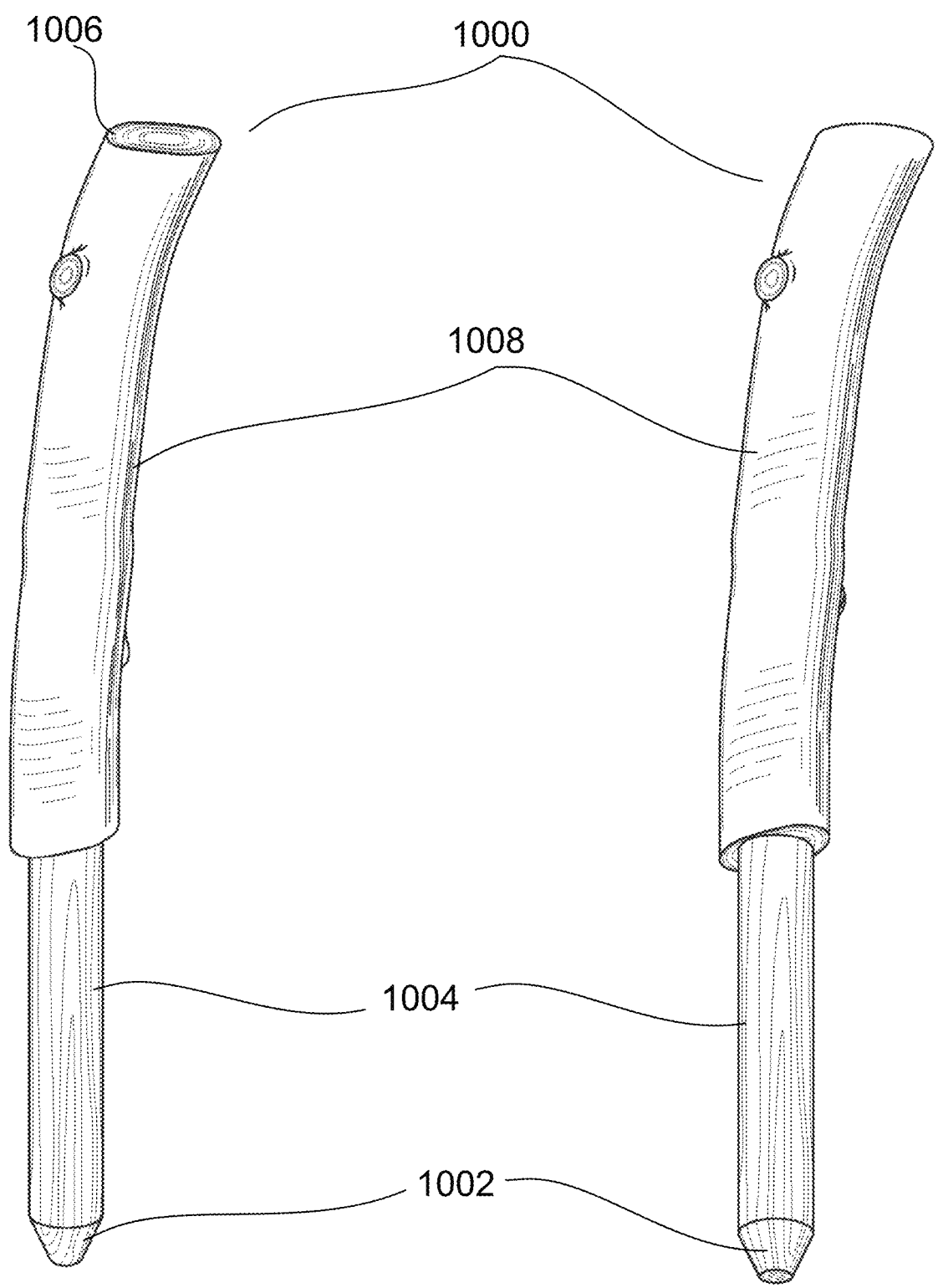
FIGS. 10A-B illustrate a formed botanical cleaning component from a botanical offshoot.

FIGS. 10A-B illustrate perspective views of a natural botanical offshoot 1000, where the insertion section 1004 has been formed by cutting away a portion of the natural offshoot and formed to a specific length having a particular diameter. The cleaning section 1008 is shown in its natural form, where it isn't necessarily a perfectly straight shaft and with the bark still on the outer surface. Once the bark is removed, the underlying surface 1006 can be used for cleaning. As noted above, this underlying surface can be further roughened prior to use. The end tip 1002 of insertion section 1004 can be further cut or formed to aid in inserting into the insertion channel of the dental cleaning assembly as noted above.

It should be noted that in some variations, the botanical cleaning component 1000 can be shipped to an end user with the bark still attached, and wherein the end user can further use a bark stripping tool. In yet another process, the botanical cleaning components 1000 can be shipped from one region with the bark still on and then additional processing is done at a distribution facility or other intermediate facility configured to finalize the processing, wherein the finalized product can be shipped to retail stores or directly to consumers. One advantage of waiting to strip the bark closer to the end user receiving the product is that the bark can help maintain higher levels of botanical juice or liquid by weight. In other words, the botanical cleaning components retain or dry-out less quickly with the bark layer still attached. In yet, another alternative method, on demand orders and timing of product use can determine when the botanical cleaning components are fully processed to ensure delivery of the natural botanical cleaning component with the desired liquid by weight ratios as noted above.

Of course, the present invention is not limited to the above features and advantages. Those of ordinary skill in the art will recognize additional features and advantages upon reading the following detailed description, and upon viewing the accompanying drawings.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

The invention claimed is:

1. A dental cleaning system comprising:
   a botanic cleaning component consisting of a twig or branch, grown from a tree, having a cleaning section that has been stripped of bark and intended to clean a user's teeth, and an insertion section that is machined to a diameter; and
   a dental cleaning assembly comprised of;
   a housing, having a power source and motor disposed therein,
   an insertion channel in mechanical communication with the motor,
   a head portion having a pair of arms, and
   an operating switch,
   wherein a portion of the insertion section of the botanic cleaning component is inserted through a front slot disposed between the pair of arms of the head portion and into the insertion channel, and wherein the machined insertion section is configured to mate with the insertion channel.

2. The dental cleaning system of claim 1, where the head portion further include a backside slot.

3. The dental cleaning system of claim 1, wherein the arms of the head portion are configured to brace a portion of the insertion section of the dental cleaning component between the arms.

4. The dental cleaning system of claim 1, wherein the dental cleaning component has a liquid portion by weight equal to or greater than 5%.

5. The dental cleaning system of claim 1, wherein the dental cleaning component has a liquid portion by weight equal to or greater than 10%.

6. The dental cleaning system of claim 1, wherein the dental cleaning component has a liquid portion by weight equal in a range of 10% to 20%.

7. The dental cleaning system of claim 1, wherein the dental cleaning component has a liquid portion by weight equal not greater than 30%.

8. The dental cleaning system of claim 1, wherein the insertion section of the dental cleaning component includes an end section that has a diameter less than the insertion section.

9. The dental cleaning system of claim 1, wherein the motor is configured to drive the dental cleaning component in a vibrating, oscillating or rotational manner.

10. The dental cleaning system of claim 9, wherein the direction of the oscillating manner includes: up and down, right to left, or in and out motions.

11. The dental cleaning system of claim 1, wherein the botanical cleaning component is formed one of the following plants: one of the varieties of Neem, one of the varieties of Eucalyptus, one of the varieties of Bamboo, and one of the varieties of Melaleucas.

12. The dental cleaning system of claim 1, wherein the cleaning section has been partially flattened from an original harvested shape.

* * * * *